United States Patent [19]

Barnea

[11] Patent Number: 4,459,990
[45] Date of Patent: Jul. 17, 1984

[54] RADIOGRAPHIC METHOD AND APPARATUS FOR THE VISUALIZATION OF THE INTERIOR OF A BODY PARTICULARLY USEFUL FOR THE VISUALIZATION OF A SUBJECT'S CIRCULATORY SYSTEM

[75] Inventor: Daniel I. Barnea, Tel-Aviv, Israel

[73] Assignee: Elscint, Incorporated, Boston, Mass.

[21] Appl. No.: 342,891

[22] Filed: Jan. 26, 1982

[51] Int. Cl.$^3$ .............................................. A61B 6/00
[52] U.S. Cl. .................................. 128/656; 128/654; 128/659; 604/20
[58] Field of Search ....................... 128/654, 656–659, 128/653, 664–666, 632–634; 604/20–21, 51–53; 250/327.2, 491.1

[56] References Cited

U.S. PATENT DOCUMENTS

| | | | |
|---|---|---|---|
| 3,500,820 | 3/1970 | Almen | 128/657 |
| 3,687,142 | 8/1972 | Leibinzohn | 128/656 X |
| 3,798,366 | 3/1974 | Hunt et al. | 128/664 X |
| 3,884,220 | 5/1975 | Hartnett | 128/654 |
| 3,975,637 | 8/1976 | Ikedo et al. | 250/327.2 |
| 4,271,842 | 6/1981 | Specht et al. | 128/661 |
| 4,294,259 | 10/1981 | Picunko et al. | 128/653 |
| 4,382,184 | 5/1983 | Wernikoff | 128/653 X |

FOREIGN PATENT DOCUMENTS

| | | | |
|---|---|---|---|
| 0526092 | 5/1977 | U.S.S.R. | 128/654 |
| 0650615 | 3/1979 | U.S.S.R. | 128/654 |

OTHER PUBLICATIONS

Vas et al., "Computer Enhancement of Direct and Venous-Injected Left Ventricular Contrast Angiography", Amer. Heart Journ., vol. 102, No. 4, 10–1981, pp. 719–728.
O'Neill et al., "Pervenous Retrieval of Embolized Catheters from the Rt. Heart and Pulmonary Arteries", Amer. Heart Journal, vol. 98, No. 1, 9–1979, pp. 287–293.

Primary Examiner—Lee S. Cohen
Assistant Examiner—Angela D. Sykes
Attorney, Agent, or Firm—Sandler & Greenblum

[57] ABSTRACT

A digital radiographic method and apparatus are described for the visualization of a portion of the circulatory system of a subject by feeding a catheter through a blood vessel while its progress is observed by exposing the respective portion of the subject's body to penetrating radiation, e.g., X-rays. In the described method and apparatus, all the prior positions of the catheter are stored so that all such prior positions visited by the catheter are displayed with each display of its current position. In addition, during the feeding of the catheter through the blood vessel, a substance relatively opaque to the radiation is injected into the blood vessel, whereby the digitized images of the previous catheter visits which are stored and displayed also include the image of the blood vessel and its junctures as revealed by the injected substance.

33 Claims, 4 Drawing Figures

RADIOGRAPHIC METHOD AND APPARATUS FOR THE VISUALIZATION OF THE INTERIOR OF A BODY PARTICULARLY USEFUL FOR THE VISUALIZATION OF A SUBJECT'S CIRCULATORY SYSTEM

BACKGROUND OF THE INVENTION

The present invention relates to a radiographic method and apparatus for the visualization of the interior of a body, and particularly to an angiographic method and apparatus for the visualization of a portion of the circulatory system of a subject by a catheterization procedure.

Angiography is a well-known technique in medical practice for the visualization of the circulatory system of the body including the heart. In the catheterization procedure, a catheter, usually a narrow flexible tube, is introduced into and fed through the blood vessel via a puncture in the wall of a peripheral artery or vein, usually while a contrast fluid is injected thereby into the blood vessel. The catheter itself is radiopaque; that is, it attenuates penetrating radiation, such as X-rays, more than the body tissues and organs into which the catheter is inserted. The progress of the catheter as it is fed through the blood vessel is thus made visible by means of radiography or fluoroscopy, and particular areas of the blood vessel can be selected for attention by the radiologist by the release of controlled quantities of the fluid from the tip of the catheter.

One of the problems commonly arising when feeding the catheter along a blood vessel e.g., to reach the heart, is the difficulty of guiding the catheter into the proper branch of the blood vessel at its branching points. With the existing techniques, this is usually achieved by trial and error; and if the catheter enters the wrong branch, it has to be withdrawn back to the junction and another attempt made, which frequently results in repeating the same error.

Another problem in the known angiographic technique arises because the blood vessel system is not static. Thus, breathing will cause a periodic displacement of the blood vessel in the vicinity of the lungs or heart, thereby tending to produce a non-stationary display which may result in a blurring and loss of definition in the displayed image.

An object of the present invention is to provide a radiographic method and apparatus for the visualization of the interior of a body, and particularly for the visualization of a subject's circulatory system, having advantages in the above respects.

BRIEF SUMMARY OF THE INVENTION

According to one aspect, the invention is applied for the visualization of a portion of the circulatory system of a subject by a procedure in which a catheter is introduced into and fed through a blood vessel of the subject while its progress is observed by exposing the respective portion of the subject's body to penetrating radiation, e.g. X-rays, and displaying the positions of the catheter. According to the invention, the novel method involves the storing of some or all the prior positions of the catheter in the subject's circulatory system during the respective procedure, and displaying the stored prior positions with the display of each current position of the catheter.

More particularly, when the method is implemented by digital radiographic techniques, the catheter is fed through the blood vessel while a plurality of exposures are made of the respective portion of the subject's body to the penetrating radiation to produce a digitized image of the catheter-produced attenuation during each exposure; the coordinate points of the digitized image of the catheter-produced attenuation are stored to produce a stored digitized image of the previous catheter visits; and, during each display of the current catheter position, there is also displayed the stored digitized image of the previous catheter visits.

According to a further aspect of the invention, during the feeding of the catheter through the blood vessel, a substance relatively opaque to the penetrating radiation may be injected into the blood vessel, whereby the digitized images of the previous catheter visits, which are stored and displayed, would also include the digitized image of the blood vessel and its junctures revealed by the injected substance.

By displaying, with each display of the current position of the catheter, the previous visits of the catheter and/or the blood vessel and its junctures as revealed by the injected substance, the practitioner is greatly aided in guiding the catheter through the proper branches of the blood vessel to the ultimate desired destination of the catheter, e.g., the patient's heart.

The above method can be easily implemented by known digital radiographic techniques, wherein the stored coordinate points of the digitized image signals of the catheter-produced attenuation, and/or the injected-substance-produced attenuation, are those exceeding a predetermined threshold value above the background or noise signals.

According to a variation, an image may first be made of the respective portion of the subject's circulatory system before the introduction of the catheter or of the injected substance, to produce a digitized image of the background-attenuation resulting from, e.g., bone and surrounding tissue. The digitized image of the background-attenuation may then be digitally subtracted from the stored images, so that the displays are substantially free of shadows of bone and surrounding tissues in the respective portions of the subject's circulatory system being visualized.

According to a further aspect of the invention, the positions of the catheter may be periodically sensed in synchronism with a cyclic function of the subject, such as the motion of the subject's chest wall or the electrical activity of the subject's heart, so that the displays of the current and prior positions of the catheter are substantially free of motion, and thereby of the blurring and loss of definition resulting from such motion.

While the invention is particularly useful for the visualization of a subject's circulatory system, it will be appreciated that the invention may be used in other applications as well. Thus, the invention may be used, e.g. by using a probe in lieu of a catheter, for the visualization of another channel in a living body, or for the visualization or mapping of the interior of artificial bodies, for example a pipe network or a hollow body.

The invention also provides apparatus particularly useful for implementing the above method.

Further features and advantages of the invention will be apparent from the description below.

BRIEF DESCRIPTION OF THE DRAWINGS

The invention is herein described, somewhat diagrammatically and by way of example only, with reference to the accompanying drawings, wherein.

DESCRIPTION OF A PREFERRED EMBODIMENT

Figure 1:
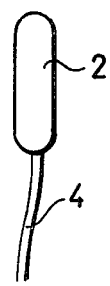
FIG. 1 illustrates one form of catheter, including means for injecting a radiation-opaque substance, useful in the method and apparatus of the present invention.
Figure 1:
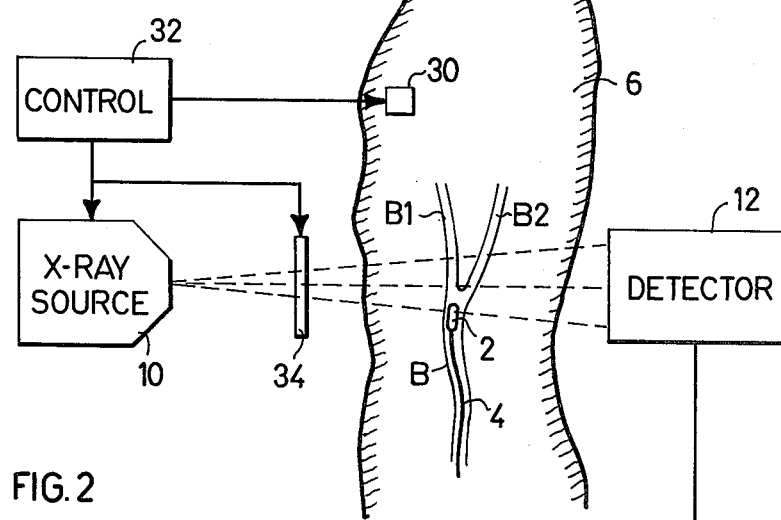

With reference to FIG. 1, there is illustrated a catheter, designated 2, of known construction which is introduced into and fed through the blood vessel via a puncture in the wall of a peripheral artery or vein. The catheter 2 itself is usually radio-opaque; i.e., it attenuates the penetrating radiation, e.g., X-rays, to a greater extent than the body tissues and organs into which it is inserted. The catheter 2 also includes a long flexible tube 4 through which a contrast substance may be fed for injection into the blood vessel. In the known catheterization procedures, a contrast fluid may be injected not only to indicate the current position of the catheter, but may also be used as a "look-ahead" to indicate the blood vessel junctures in front of the catheter. In the known procedures, however, the injected substance is quickly washed away by the blood flowing through the blood vessels, and therefore this indication of the vessel junctures is provided only for an instant and quickly disappears from the display.

Figure 2:
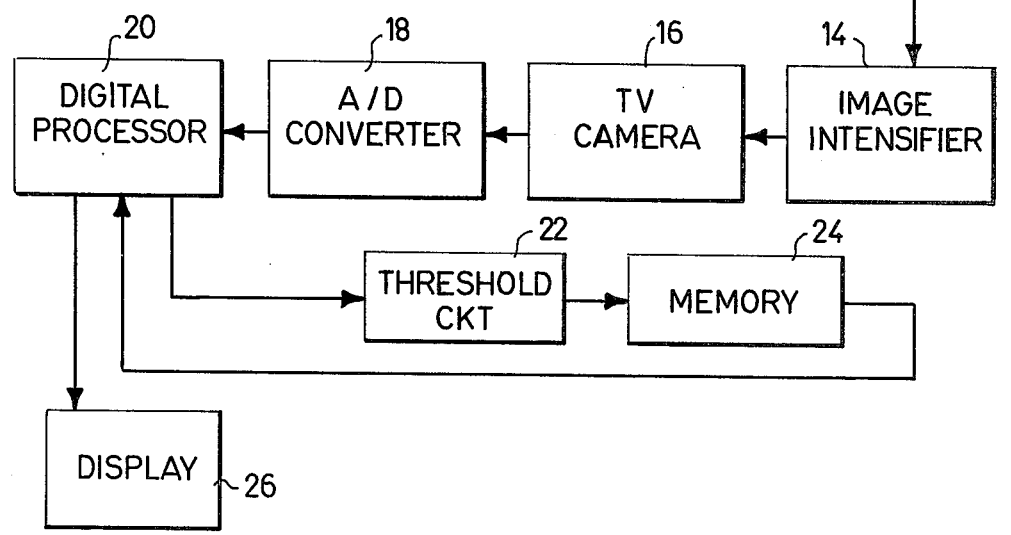
FIG. 2 is a block diagram illustrating one form of apparatus constructed in accordance with the invention.

FIG. 2 illustrates a subject 6 undergoing a catheterization procedure in which the catheter 2 is fed through a blood vessel B of the subject while the subject's body is exposed to penetrating radiation from, e.g., a source of X-rays 10, disposed on one side of the subject. At the opposite side of the subject, there is provided a detector 12, such as of the scintillation crystal type, which detects the attenuated X-rays leaving the subject's body and converts the X-ray image to a light image. This light image is intensified in an image-intensifier 14, and is fed to a TV camera 16, which scans the image and outputs an electrical signal corresponding to an analogue representation of the light image. This electrical signal is outputted to an analogue-to-digital converter 18 which digitally encodes this information, both position and amplitude, and feeds same to a digital data processor 20.

Digital data processor 20 determines, by means of a threshold comparator circuit 22, which of the foregoing information exceeds a predetermined threshold value. This threshold value is above the background-produced attenuation, but below the catheter-produced attenuation and the injected-substance-produced attenuation, so that the information outputted from the threshold comparator 22 is free of the background-produced attenuation, but includes the catheter-produced and the injected-substance-produced attenuation. The latter information is transferred via the threshold comparator 22 to a memory 24, where it is stored.

Digital processor 20 controls a video display unit 26 for displaying the current position of the catheter during each exposure by the X-ray source 10. With each display of the current position of the catheter, the information stored in memory 24 is also displayed in the display unit 26. Thus each such display of the current position of the catheter also includes: (1) a display of all the prior visits of the catheter produced by the stored coordinate points of the catheter-produced attenuation digitized image; and (2) a display of the blood vessel and its junctures produced by the stored coordinate points of the digitized image of the injected-substance-produced attenuation.

Thus, with each display of the current position of the catheter the practitioner also sees a display of all the prior visits of the catheter, and also a mapping of the blood vessel and its junctures, both of which greatly aid him in guiding the catheter through the proper branches of the blood vessel to the desired destination.

The apparatus illustrated in FIG. 2 further includes a sensor, designated 30, for monitoring a cyclic function of the subject, such as the subject's breathing activity or the electrical activity of the subject's heart. Sensor 30 controls a trigger-pulse generator 32 generating a trigger-pulse in synchronism with the monitored cyclic function of the subject. This trigger-pulse is used to control the energization of the X-ray source 10, as shown schematically in FIG. 1, and/or to control a shutter, schematically indicated at 34, between the subject's body and the X-ray source.

For example, if the breathing function of the subject is being monitored, sensor 30 could sense the instant of minimum velocity of the subject's chest wall, or the instant of its maximum displacement in a particular direction, so that the digital processor 20 would receive, store and process only the X-ray image information generated at that instant. Thus, the display produced in the video display unit 26 would be relatively free of motion, thereby also freeing the display of possible blurring, smear or loss of definition resulting from such image motion.

Sensor 30, instead of synchronizing the apparatus with the breathing function of the subject, could also synchronize it with the electrical activity of the subject's heart, in like manner as described above.

The method and apparatus described above are preferably used in accordance with the "frame subtraction" technique, wherein a reference digitized image of the body is made before the introduction of the catheter or of the relatively opaque substance, and the reference digitized image so made is digitally subtracted in the data processor unit 20 from the images made after the introduction of the catheter and opaque substance. Thus, the display in unit 26 of all the prior positions of the catheter with each display of its current position, would be substantially free of the shadows of bone and surrounding tissues in the system being visualized.

Figure 3:
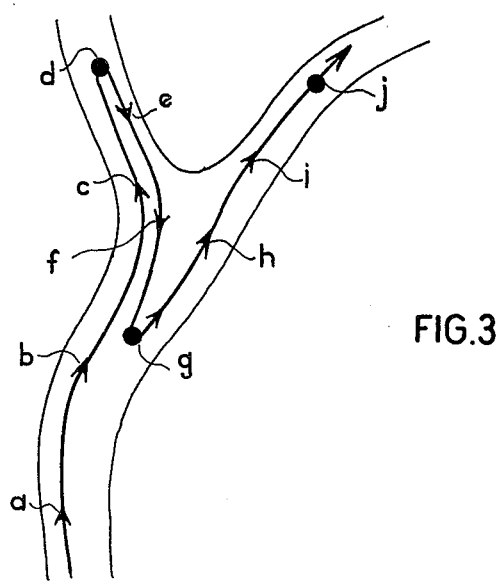
FIG. 3 schematically illustrates the successive positions of the tip of a catheter as it is fed through a blood vessel during a catheterization procedure in accordance with the invention.
Figure 4:
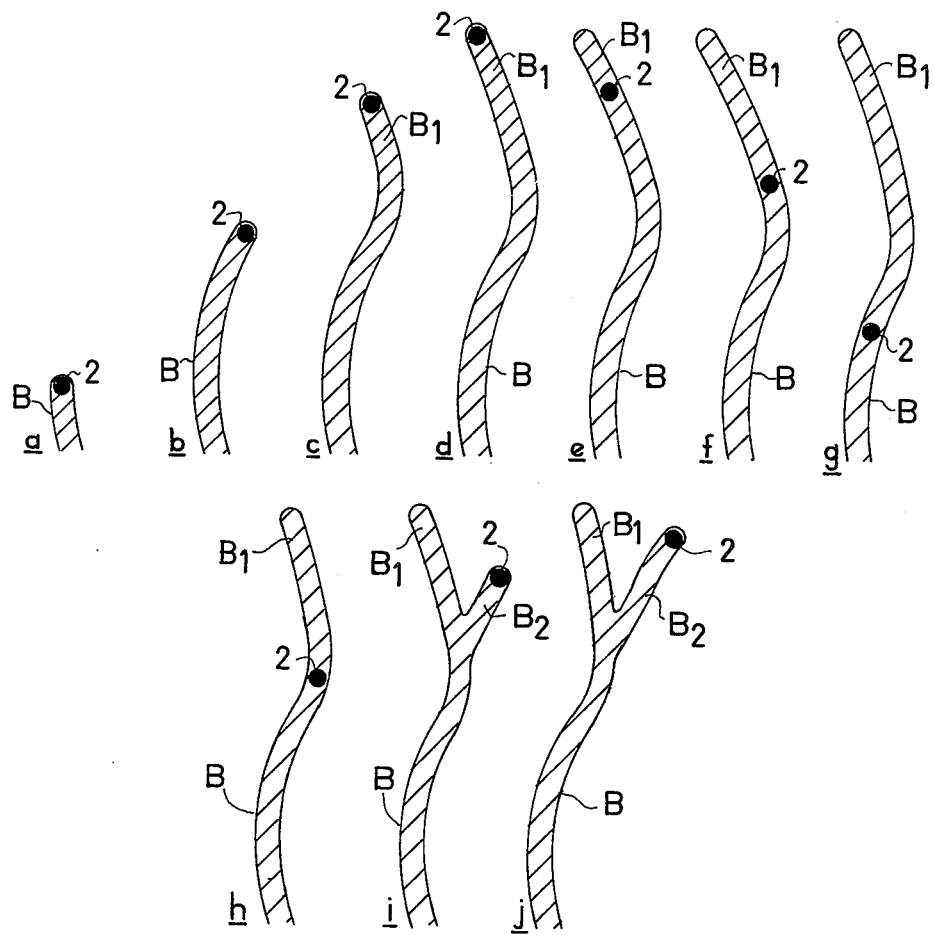
FIG. 4 illustrates the successive display frames produced in accordance with the method and apparatus illustrated in FIG. 2, for displaying all the prior positions of the catheter as illustrated in FIG. 3 with each current position, in order to aid the practitioner in guiding the catheter to the desired ultimate destination.

FIG. 3 illustrates the progress of the catheter 2, particularly of its tip, as it is fed through successive locations in the blood vessel B just before and after a branch juncture $B_1$, $B_2$ in the blood vessel, while FIG. 4 illustrates the successive display frames that would be presented in the display unit 26.

Thus, as shown in FIGS. 3 and 4, as the catheter was moved from locations "a" through "d" of the blood vessel B, it passed the juncture (at location "c") of the blood vessel according to an incorrect route, namely, entering branch $B_1$, whereas it should have entered branch $B_2$. This was not discovered until the catheter tip had already advanced to location "d", whereupon it was withdrawn back through the branch point (location "c") and through locations "e", "f", and "g", and then re-manipulated to and through the correct branch $B_2$, as shown by the catheter tip progressing through locations "h"–"j".

The portion of the blood vessel B and the juncture of its branches $B_1$, $B_2$ traversed by the catheter, or just in front of the catheter before traversing same, as revealed by the injected radio-opaque substance, are also stored and displayed with each display of the current position of the catheter.

The display of the prior "visits" of the catheter (i.e., through the wrong branch $B_1$) and/or of the blood vessel and its junctures, with the display of each current position of the catheter, greatly aids the practitioner in manipulating the catheter through the correct branch $B_2$ and not through the erroneous branch path $B_1$.

The above-described procedure can be conveniently depicted in mathematical terms. Thus, if (x,y) is a point in the coordinate system of the X-ray object plane, then f(x,y) represents the image density function in the absence of catheter or radio-opaque fluid (i.e., the digitized image of the background produced attenuation) as stored and displayed by the computerized radiography system. The presence of the catheter and/or radio-opaque injected substance will produce a new image density function f(x,y)+g(x,y) where g(x,y) represents the change in f(x,y) resulting from the presence of the catheter and/or the injected radio-opaque substance. It is required that $$g(x,y) \geq b \text{ for all } (x,y)$$

where "b" represents the predetermined threshold above the background information to be stored and to be displayed with each display of the current position of the catheter.

We define a set of points "V" which is the projection in the imaging plane of all the points which are internal points of the vessel system. We also define another set of points "U", part of "V", which is the set of all points which, during the history of the process, have been "visited" by the catheter or by the radio-opaque substance that has been ejected from its tip. That is, "U" defines the set of all points before time "t"; time "t" is any particular instant of time. The recognition of such a "visit" at (x,y) is defined such that at some time t, g(x,y)>b and U(x,y,t) includes U(x,y,t') for all t'≦t. If K(x,y) is defined as 0 when (x,y)∉U, and K when (x,y)∈U, then the function displayed is: f(x,y)+g(x,y)+K(x,y).

It will be appreciated that many variations and modifications of the invention may be made. For example, the background (bone, tissue, etc.), if displayed at all, can be displayed very faintly, the current position of the catheter displayed strongly, and the previous visits of the catheter, together with the blood vessel and its junctures, displayed at an intermediate level. Instead of different levels of grey, the displays may be of different colors with a distinctive hue reserved for k(x,y). Further, the invention may be used in other applications, for example, in the visualization of other channels of a living body, or in the visualization or mapping of the interior of artificial bodies, such as a piping network, wherein there would be used, instead of the catheter, a probe which was radio-opaque and/or injected a substance which was radio-opaque.

Many other variations, modifications and applications of the invention will be apparent.

What is claimed is:

1. A method for visualizing a portion of the circulatory system of a subject by a procedure in which a catheter is introduced into and fed through a blood vessel of the subject while the progress of the catheter is observed in a display obtained by sequentially exposing said portion to penetrating radiation to obtain sequential images of the catheter and by sequentially displaying individual ones of the obtained images, the image last obtained representing the current position of the catheter and the previously obtained images representing previous positions of the catheter during its progress to the current position, the improvement comprising the steps of:
   storing the sequentially obtained images; and
   superimposing said sequentially obtained images in a single display.

2. The method according to claim 1, wherein said previous positions of the catheter are stored by digitally encoding such previous positions and storing them in a digital data processor.

3. A method for visualizing a portion of the circulatory system of a subject comprising the steps:
   feeding a catheter through a blood vessel in said portion of the circulatory system while making a plurality of exposures of said portion to penetrating radiation to produce a digitized image of the catheter-produced attenuation during each exposure;
   storing coordinate points of the digitized image of the catheter-produced attenuation to produce a stored digitized image of the progress of the catheter through the circulatory system; and
   superimposing on a display, the digitized image of the catheter-produced attenuation during the last exposure and the stored digitized image of previously obtained exposures.

4. The method according to claim 3, wherein during the feeding of the catheter through the blood vessel, a substance relatively opaque to the penetrating radiation is injected into the blood vessel, whereby the digitized image of the previous catheter visits which is stored and displayed also includes the image of the blood vessel and its junctures revealed by the injected opaque substance.

5. The method according to claims 3 or 4, wherein positions of the catheter are periodically sensed in synchronism with the motion of the subject's chest wall.

6. The method according to claims 3 or 4, wherein positions of the catheter are periodically sensed in synchronism with the electrical activity of the subject's heart.

7. The method according to claim 4, wherein the coordinate points of the catheter-produced attenuation digitized image which are stored are those exceeding a predetermined threshold value.

8. The method according to claims 3, 4 or 5, further characterized in that:
   an image is first made of the respective portion of the subject's circulatory system before the introduction of the catheter to produce a digitized image of the background-attenuation resulting from bone and surrounding tissue;

and the digitized image of the background-attenuation is digitally subtracted from the images displayed, whereby the displays are substantially free of shadows of bone and surrounding tissues in the respective portion of the subject's circulatory system being visualized.

9. The method according to claims 3, 4 or 5, further characterized in that positions of the catheter are periodically sensed and stored in synchronism with a cyclic function of the subject, whereby the displays of the current and prior positions of the catheter are substantially free of motion normally produced by body movements.

10. The method according to claim 3, wherein the respective portion of the subject's body is exposed to X-rays, and is displayed by detecting the attenuated X-rays exiting from the respective portion of the subject's body.

11. A method for the visualization of a respective portion of the circulatory system of a subject, comprising the steps:

feeding a catheter through a blood vessel in the respective portion of the subject's circulatory system and injecting a substance relatively opaque to penetrating radiation while making a plurality of exposures of the respective portion of the subject's body to the penetrating radiation to produce a digitized image of the radiation-attenuation, during each exposure, caused by the injected substance;

storing coordinate points of the radiation-attenuation digitized image to produce a stored digitized image of the blood vessel and its junctures;

and displaying, during each of said exposures, the digitized image of the radiation-attenuation during the respective exposure, together with the stored digitized image of the blood vessel and its junctures.

12. The method according to claim 11, wherein coordinate points of the catheter-produced attenuation during each exposure are also stored to produce stored digitized image of previous catheter visits, which latter stored images are also displayed with the display of the image of the blood vessel and its junctures.

13. A method for the visualization of a channel in a body, comprising the steps:

feeding a probe through the body channel while making a plurality of exposures of the body to penetrating radiation to produce a digitized image of the probe-produced attenuation during each exposure;

storing coordinate points of the digitized image of the probe-produced attenuation to produce a stored digitized image of previous probe visits;

and displaying, during each of said exposures, the digitized image of the probe-produced attenuation during the respective exposure together with the stored digitized image of previous probe visits.

14. The method according to claim 13, wherein, during the feeding of the probe through the body channel, a substance relatively opaque to the penetrating radiation is injected into the body channel, whereby the digitized image of the previous probe visits which is stored and displayed also includes the image of the body channel and its junctures revealed by the injected opaque substance.

15. The method according to claim 14, wherein coordinate points of the probe-produced attenuation digitized image which are stored are those exceeding a predetermined threshold value.

16. The method according to claim 13, further characterized in that:

an image is first made of the respective portion of the body channel before the introduction of the probe to produce a digitized image of the background-attenuation;

and the digitized image of the background-attenuation is digitally subtracted from the images displayed, whereby the displays are substantially free of the background in the body channel being visualized.

17. Apparatus for the visualization of a respective portion of the circulatory system of a subject by a procedure in which a catheter adapted to be fed through a blood vessel of a subject while its progress is observed by exposing the respective portion of the subject's body to penetrating radiation and displaying the current positions of the catheter, characterized in that said apparatus includes:

means for storing prior positions of the catheter in the subject's circulatory system during the respective procedure; and means for displaying at least some of said prior positions together with the display of each current position of the catheter.

18. Apparatus according to claim 17, wherein said means for storing prior positions of the catheter comprises a digital data processor including digital encoding means for digitizing said prior positions, and memory means for storing said digitized prior positions.

19. Apparatus according to claim 18, wherein said digital data processor further includes means for producing triggering pulses related in time with a cyclic function of the subject's body, and means controlled by said triggering pulses for controlling the exposure of the subject's body to said radiations, whereby the displays of the current positions of the catheter are free of movement normally arising because of body movements.

20. Apparatus according to claim 14, wherein said means for producing the triggering pulses includes a sensor means for sensing the motion of the subject's chest wall.

21. Apparatus according to claim 19, wherein said means for producing the triggering pulses includes a sensor means for sensing the electrical activity of the subject's heart.

22. Apparatus according to claim 19, wherein said triggering pulses control the energization of the penetrating radiation source.

23. Apparatus according to claim 19, wherein said triggering pulses control a shutter between the subject's body and said penetrating radiation source.

24. Apparatus for the visualization of a respective portion of the circulatory system of a subject, comprising:

a source of penetrating radiation for exposing the respective portion of the subject's body;

radiation-detector means for detecting the radiation leaving the respective portion of the subject's body to produce a digitized image indicating the attenuation suffered by the radiation when passing through the subject's body;

a catheter adapted to be fed through a blood vessel in the respective portion of the subject's circulatory system while making a plurality of exposures of the respective portion of the subject's body to the penetrating radiation to produce a digitized image of the catheter-produced attenuation during each exposure;

a digital processor including storing means for storing coordinate points of the catheter-produced attenuation digitized image to produce a stored digitized image of previous catheter visits;

and display means for displaying, during each exposure, the digitized image of the catheter-produced attenuation during the respective exposure to indicate the current position of the catheter, together with the stored digitized image of the previous catheter visits.

25. Apparatus according to claim 24, wherein said storing means stores only the coordinate points of the catheter-produced attenuation digitized image exceeding a predetermined threshold value above the background attenuation.

26. Apparatus according to claim 25, wherein said catheter includes means for injecting therethrough into the blood vessel a substance relatively opaque to the penetrating radiation, whereby the digitized image of the previous catheter visits which is stored and displayed also includes the image of the blood vessel and its junctures revealed by the injected opaque substance.

27. Apparatus according to claim 24, further including means for digitally subtracting a digitized image of the background attenuation resulting from bone and surrounding tissue from the images displayed, whereby the displays of the current catheter position are substantially free of shadows of bone and surrounding tissues in the respective portion of the subject's circulatory system being visualized.

28. Apparatus according to claim 24, wherein said penetrating radiation source is a source of X-rays.

29. Apparatus for the visualization of a respective portion of the circulatory system of a subject, comprising:

a source of penetrating radiation for exposing the respective portion of the subject's body;

radiation-detector means for detecting the penetrating radiation leaving the respective portion of the subject's body to produce a digitized image indicating the attenuation suffered by the radiation when passing through the subject's body;

a catheter adapted to be fed through a blood vessel in the respective portion of the subject's circulatory system while making a plurality of exposures of the respective portion of the subject's body to the penetrating radiation, said catheter including means for injecting therethrough into the blood vessel a substance relatively opaque to the penetrating radiation to produce a digitized image of the blood vessel and its junctures revealed by the injected opaque substance;

a digital processor including storing means for storing coordinate points of the digitized image of the blood vessel and its junctures;

and display means for displaying, during each exposure, the digitized image of the catheter-produced attenuation during the respective exposure, together with the stored digitized image of the blood vessel and its junctures.

30. Apparatus according to claim 29, wherein said storing means also stores coordinate points of the catheter-produced attenuation during each exposure to produce stored digitized images of previous catheter visits, which latter stored images are also displayed with the display of the image of the blood vessel and its junctures.

31. Apparatus for the visualization of a channel in a body, comprising:

a source of penetrating radiation for exposing the body;

radiation-detector means for detecting the radiation leaving the body to produce a digitized image indicating the attenuation suffered by the radiation when passing through the body;

a probe adapted to be fed through the channel in the body while making a plurality of exposures of the body to the penetrating radiation to produce a digitized image of probe-produced attenuation during each exposure;

a digital processor including storing means for storing coordinate points of the probe-produced attenuation digitized image to produce stored digitized images of previous probe visits;

and display means for displaying, during each exposure, the digitized image of the probe-produced attenuation during the respective exposure to indicate the current position of the probe, together with the stored digitized images of the previous probe visits.

32. Apparatus according to claim 31, wherein said storing means stores only the coordinate points of the probe-produced attenuation digitized image exceeding a predetermined threshold value above the background attenuation.

33. Apparatus according to claim 31, wherein said probe includes means for injecting therethrough into the body channel a substance relatively opaque to the penetrating radiation, whereby the digitized images of the previous probe visits which are stored and displayed also include the images of the body channel and its junctures revealed by the injected opaque substance.

* * * * *